United States Patent

Schulz et al.

Patent Number: 6,019,719
Date of Patent: Feb. 1, 2000

[54] FULLY AUTOCLAVABLE ELECTRONIC ENDOSCOPE

[75] Inventors: Dieter Schulz, Muehlheim; Rainer Brunnen, Seitingen-Oberflacht; Norbert Haeckl, Leibertingen, all of Germany

[73] Assignee: Henke-Sass Wolf GmbH, Tuttlingen, Germany

[21] Appl. No.: 08/972,612

[22] Filed: Nov. 18, 1997

[30] Foreign Application Priority Data

Nov. 19, 1996 [DE] Germany .......................... 196 47 855

[51] Int. Cl.⁷ ........................................ A61B 1/05
[52] U.S. Cl. .................... 600/109; 600/129; 600/172; 600/175; 600/139
[58] Field of Search ................... 600/109, 121, 600/127, 129, 130, 140, 172, 175, 176, 181, 139

[56] References Cited

U.S. PATENT DOCUMENTS

| | | |
|---|---|---|
| 4,253,447 | 3/1981 | Moore et al. . |
| 4,261,344 | 4/1981 | Moore et al. . |
| 4,562,831 | 1/1986 | Marakoshi et al. ............. 600/109 |
| 4,685,451 | 8/1987 | Ando ............................... 600/181 |
| 4,882,619 | 11/1989 | Hasegawa et al. ............. 600/181 |
| 4,905,668 | 3/1990 | Ohsawa ........................... 600/167 |
| 4,916,534 | 4/1990 | Takahshi et al. ............... 600/171 |
| 5,305,736 | 4/1994 | Ito ................................... 600/109 |
| 5,325,847 | 7/1994 | Matsuno .......................... 600/109 |
| 5,341,240 | 8/1994 | Broome ........................... 600/163 |
| 5,427,087 | 6/1995 | Ito et al. .......................... 600/129 |
| 5,495,286 | 2/1996 | Adair ............................... 600/109 |
| 5,575,757 | 11/1996 | Kennedy et al. ............... 600/109 |
| 5,605,532 | 2/1997 | Schermehorn .................. 600/169 |
| 5,685,823 | 11/1997 | Ito et al. .......................... 600/129 |
| 5,711,756 | 1/1998 | Chikawa ......................... 600/129 |
| 5,773,244 | 3/1996 | Yasui et al. ..................... 600/129 |

FOREIGN PATENT DOCUMENTS

| | | |
|---|---|---|
| 40 15 633 | 11/1990 | Germany . |
| 39 21 233 | 2/1991 | Germany . |
| 8-256976 | 8/1996 | Japan . |
| WO 94/23539 | 10/1994 | WIPO . |

*Primary Examiner*—Gene Mancene
*Assistant Examiner*—Ira Hatton
*Attorney, Agent, or Firm*—McAulay Nissen Goldberg Kiel & Hand LLP

[57] ABSTRACT

An electronic endoscope with a semiconductor image sensor (CCD chip) for receiving the images received by an objective and with an The electronic circuit, wherein the endoscope substantially comprises a shaft with a distal end and a proximal end, and the objective and CCD chip are arranged at the distal end, and the proximal end is held in a housing which holds the shaft and encloses the glass-fiber optical connection. The electronic endoscope is wherein the component parts of the CCD chip unit arranged behind the objective, namely the crystal filter, IR cutoff filter and CCD chip, are arranged so as to be spaced from one another.

10 Claims, 6 Drawing Sheets

FIG. 1a
FIG. 1b
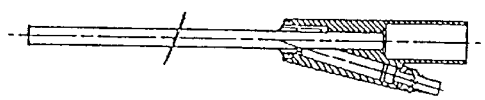
FIG. 1c

FIG. 1i  FIG. 1h

6,019,719

FULLY AUTOCLAVABLE ELECTRONIC ENDOSCOPE

BACKGROUND OF THE INVENTION a) Field of the Invention

The invention is directed to an electronic endoscope with a semiconductor image sensor (CCD chip) for receiving the images received by an objective lens and with an electronic circuit, wherein the endoscope substantially comprises a shaft with a distal and a proximal end, and the objective lens and CCD chip are arranged at the distal end, and the proximal end is held in a housing which holds the shaft and encloses the glass-fiber optical connection.

b) Description of the Related Art

An electronic endoscope of this type is known, for example, from German Patent 39 21 233 and from U.S. Pat. No. 4,253,447 or U.S. Pat. No. 4,261,344.

Such endoscopes, which are used particularly in the field of medicine, must be sterilized after using and in preparation for reuse, especially in their distal area which is introduced into the human body.

In spite of the way in which the previously known endoscopes and CCD chips were constructed and specially arranged inside the endoscope shaft, it is not possible to subject these instruments to autoclaving in their entirety, i.e., they do not withstand for long periods the minimum temperature of 134° C. which is used for this purpose. The reason for this is that the CCD chip unit, which is constructed of a plurality of parts and whose individual structural component parts are glued together and held in a metallic element, becomes "fogged" after several autoclaving processes, namely in that, owing to the temperature increase during autoclaving and the subsequent cooling, the surfaces of the individual parts, especially those of the crystal filter arranged in front of the actual CCD chip and of the IR cutoff filter, deteriorate in quality since the glue applied between their respective adjacent surfaces loses its transparency and becomes opaque.

OBJECT AND SUMMARY OF THE INVENTION

Therefore, it is the primary object of this invention to provide an endoscope which can be used particularly in the field of medicine, is fully autoclavable and remains undamaged even after frequent autoclaving processes at a temperature of 134° C. for a period of seven minutes at a pressure of 2.3 bar and at approximately 95% air humidity (saturated water vapor).

This object is met in the electronic endoscope described above in that the component parts of the semiconductor image sensor (CCD chip unit) arranged behind the objective, namely the crystal filter, IR cutoff filter and CCD chip, are arranged so as to be spaced from one another. This special construction of the CCD chip unit ensures that the surfaces of the above-named component parts facing one another do not come into contact with one another and the respective component parts therefore need not be glued together and, consequently, there is also no deterioration of quality of the CCD chip unit due to changes in the glue material when the endoscope is subjected to autoclave conditions.

The component parts of the CCD chip unit are advantageously held in a metal enclosure which forms a component part of the unit and is adjoined by a board having the cable which carries the video signal.

Due to the different extension or expansion of the CCD chip unit compared with the rest of the component parts, it is advantageous when this CCD chip unit is held at the distal end of a separately constructed CCD tube in such a way that it can change with respect to its arrangement when the autoclaving process is carried out, but can also be restored to the predetermined position, in particular also relative to the objective unit of the endoscope, after autoclaving.

For this purpose, in an advantageous further development of the invention, the distal end of the CCD tube has resilient or flexible tongues between which the CCD chip unit is installed and by which it is held in a springing elastic manner.

In a further advantageous construction of the endoscope, the shaft has various tubes, including the CCD tube, in each instance having small diameters which are adapted to one another and being insertable one inside the other and, where appropriate, displaceable relative to one another. By partitioning the interior of the shaft of the endoscope in this way, the individual structural component parts arranged at the distal end of the endoscope, such as the CCD chip unit, objective unit and the flat glass terminating the latter, can be fastened in different tubes which can then be constructed corresponding to individual requirements, for example, with respect to their tightness relative to the overall endoscope.

In addition, the tubes include a CCD tube which holds the CCD chip at its distal end in a resilient manner and also contains the cables carrying the video signals, an objective tube of larger diameter at whose distal end the objective unit is arranged, the CCD tube being mounted in the objective tube so as to be longitudinally displaceable, and a jacket tube of still larger diameter which receives the CCD tube and the objective tube and which has a terminating glass arranged at its distal end.

The configuration of these three tubes ensures that they are, in their entirety, completely tight against the penetration of air and moisture relative to the shaft of the endoscope formed by an outer tube and also relative to the housing of the endoscope and is also closed relative to the annular intermediate space which is formed between the jacket tube on the one hand and the shaft, this intermediate space receiving the light-conducting fibers serving to transmit light In addition, the terminating glass at the distal end of the jacket tube is soldered in securely and tightly by means of a special solder at 800° C. under a high vacuum.

In an advantageous further development of the invention, the jacket tube is constructed at its proximal end as a connecting socket and this connecting socket is fastened in a housing socket which is formed at the proximal end of the jacket tube, wherein the housing socket is closed tightly toward the outside by a ceramic insertion socket system.

Finally, it is provided that each of the individual surfaces of the structural component parts of the CCD chip unit is outfitted with an anti-reflection agent coating.

An embodiment example of the fully autoclavable endoscope which does not limit the invention is explained with reference to the drawings and Figures indicated in more detail hereinafter.

DESCRIPTION OF THE PREFERRED EMBODIMENTS

Figure 1D:
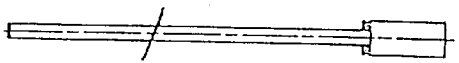
FIG. 1 shows the overall assembly in illustrations a) through i) showing the component parts of the endoscope individually and in their respective construction.
Figure 1E:
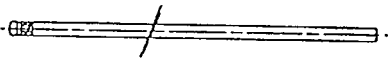
Figure 1F:
Figure 1G:
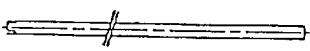
Figure 2:
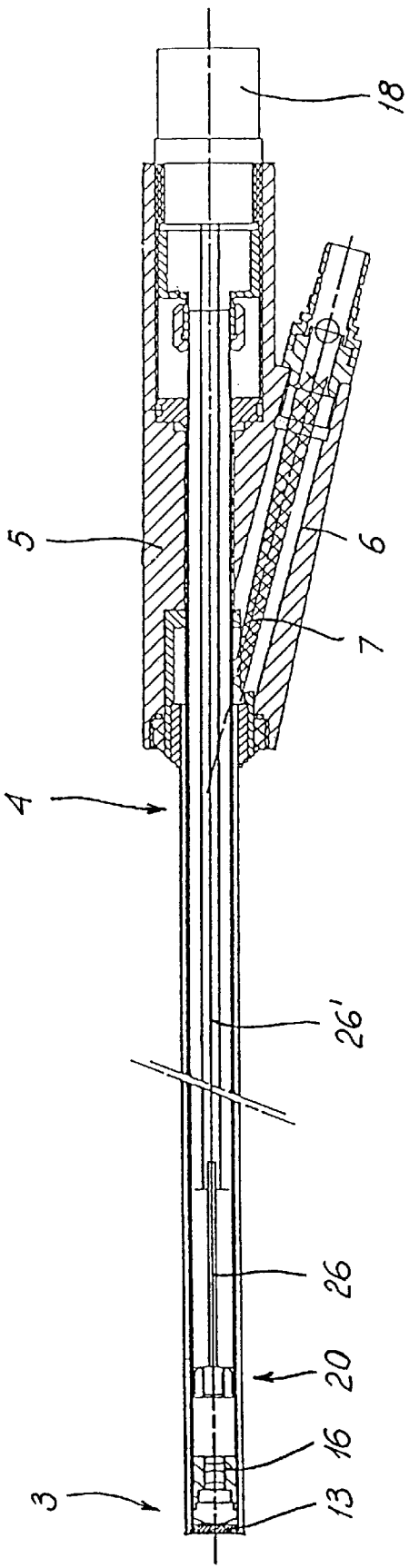
FIG. 2 shows a section through the completely assembled autoclavable endoscope according to illustration a) in FIG. 1.

The fully autoclavable endoscope shown in the Figures is provided particularly for use in the field of medicine and comprises first an outer tube 2 which forms the shaft 1 and has a distal end 3 and a proximal end 4 which is held in housing 5. The housing 5 itself, as can be seen particularly in FIG. 3, has a connection 6 for the light guide glass-fiber system to an external light source. The light-conducting glass fibers 7 are arranged in this connection 6 and are introduced into the shaft 1 in the housing 5, namely in such a way that they fill an intermediate space 9 that is formed between the outer tube 2 and another tube 8 which is arranged therein and which has a smaller diameter, and are guided from the housing 5 to the distal end 3 of the shaft 1 so that the light required at that location to illuminate the area to be observed can exit. The housing 5 in turn has, at its proximal end, a bore hole 10 which is provided for receiving corresponding devices formed on the proximal ends of the additional tubes which will be described more fully hereinafter and which are to be inserted into the shaft 1 of the endoscope.

Figure 3:
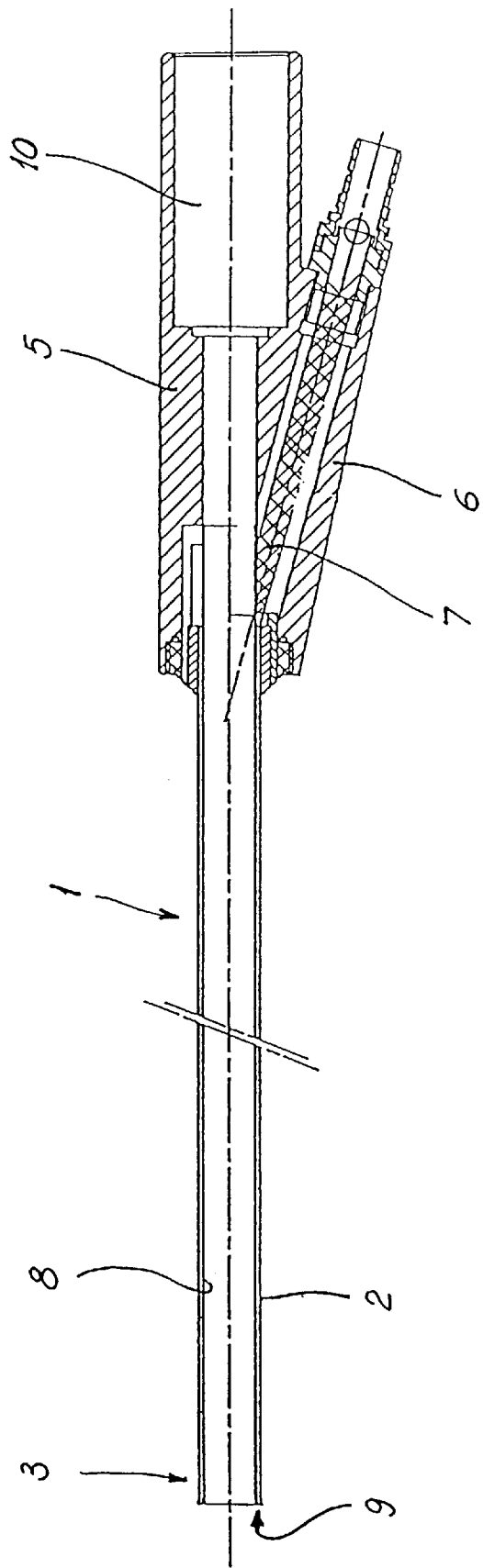
FIG. 3 shows a section through the shaft and housing of the endoscope according to illustration b) in FIG. 1.
Figure 4:
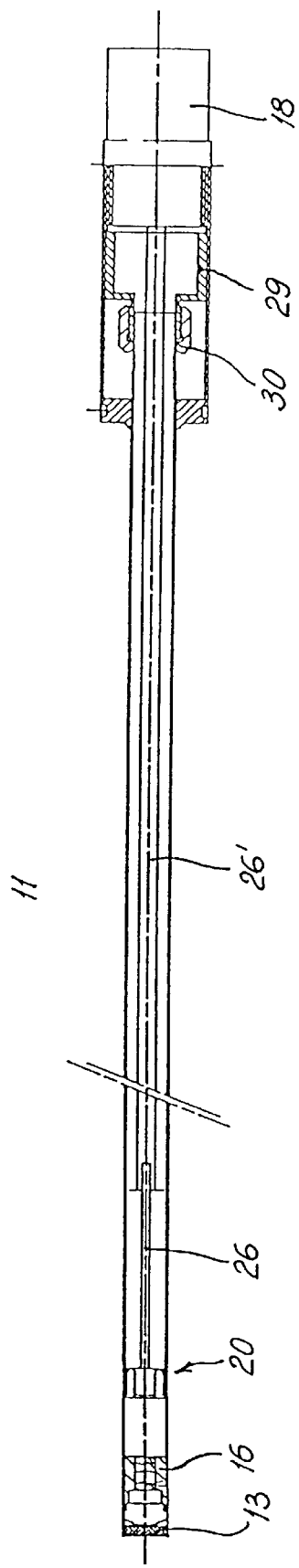
FIG. 4 shows a section though the autoclavable CCD unit and optics unit according to illustration c) in FIG. 1 comprising the additional component parts of the endoscope shown in illustrations b), e), g) and h)

The autoclavable CCD unit and optics unit 11 shown in FIG. 4 is inserted and slid into this shaft 1 shown in FIG. 3 and into the housing 5 and bore hole 10 from the proximal end of the endoscope.

Figure 6:
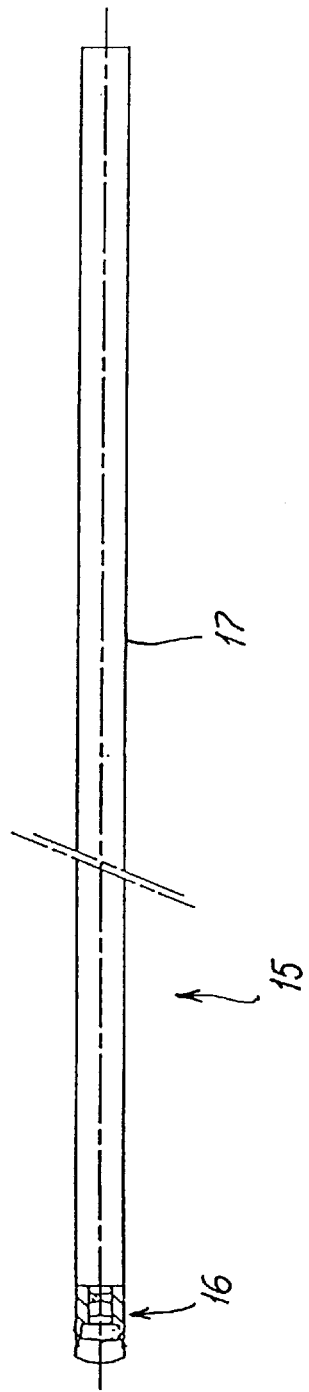
FIG. 6 shows a section through the objective tube with objective unit according to illustration e) in FIG. 1.
Figure 7:
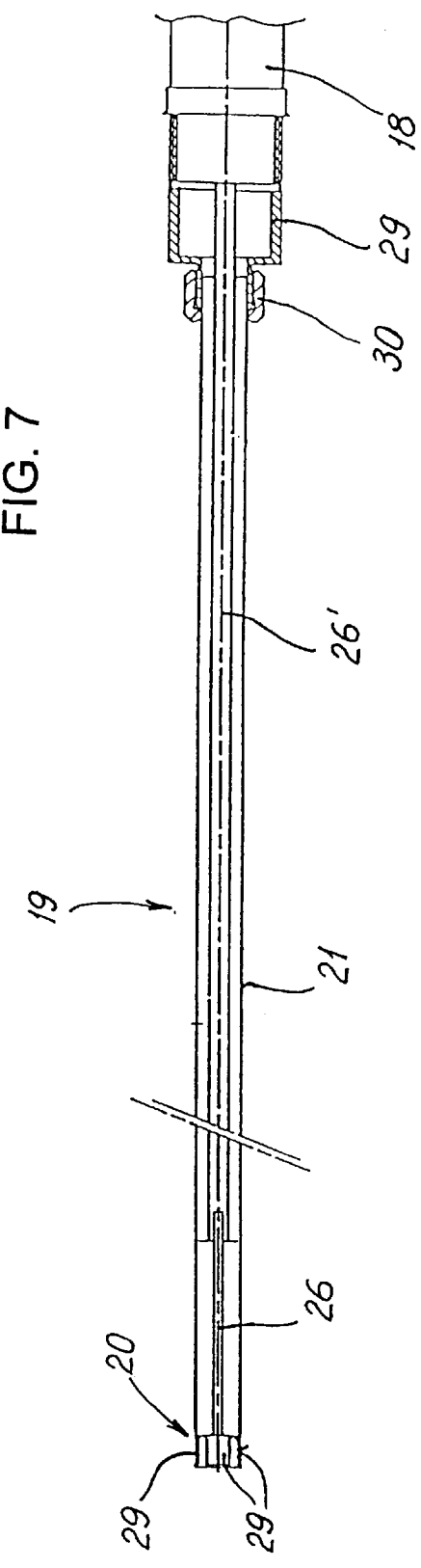
FIG. 7 shows a section according to illustration f) in FIG. 1 relating to the structural component part comprising the CCD tube and CCD chip shown in illustrations g) and h) and having the connection socket.
Figure 8:
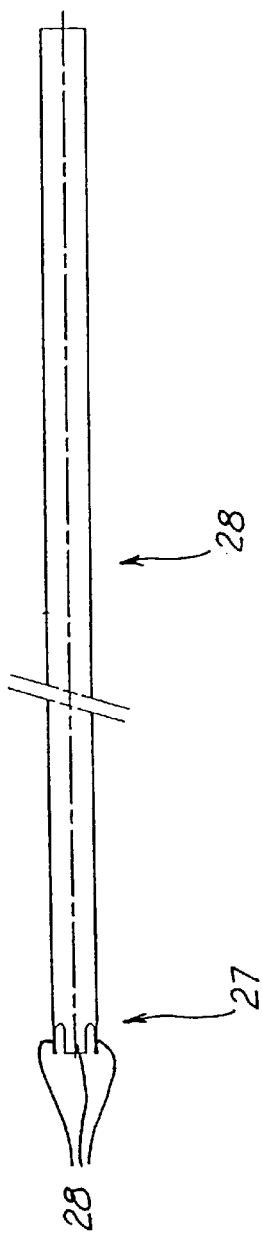
FIG. 8 shows a section through the CCD tube.
Figure 9:
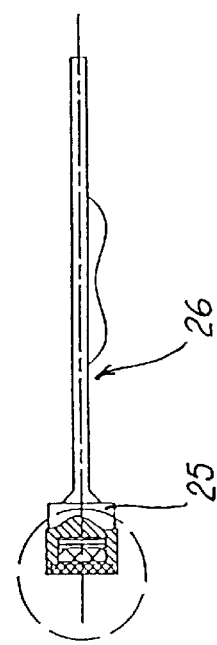
FIG. 9 shows an enlarged section through the complete CCD chip unit according to illustration h) in FIG. 1.

This autoclavable unit 11 shown in FIG. 4 substantially comprises the following: the jacket tube 12, shown in FIG. 6, with flat glass 13 and housing socket 14, the objective unit 15, shown in FIG. 6, which is inserted therein and which has an objective 16 and objective tube 17, and the CCD-chip tube unit 19, shown in FIG. 7, which is inserted in the latter and provided with a connection socket 18 and has the CCD chip 20 and CCD tube 21 which are shown in FIGS. 8 and 9. These individual component parts are shown especially clearly with respect to their interaction in FIG. 1 and in the individual illustrations c) to h) in FIG. 1.

In order to describe the construction of the autoclavable CCD unit and optics unit 11 more fully, the construction of the CCD chip unit 20 itself will be described first, followed by a description of its arrangement in the CCD tube 21 and further in the objective tube 17 and in the jacket tube 12.

Figure 10:
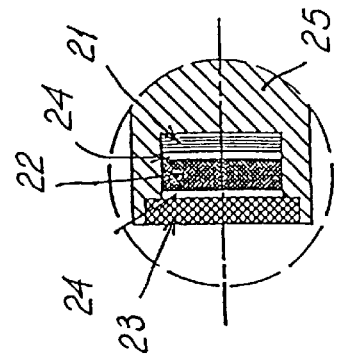
FIG. 10 shows an enlarged detail according to illustration i) in FIG. 1 in accordance with FIG. 9.

The CCD chip unit 20 is shown in FIG. 9 in an enlarged view relative to the other Figures and is shown in FIG. 10 in an enlarged view relative to FIG. 9.

The CCD chip unit 19 substantially comprises the CCD chip 21 itself, an IR cutoff filter 22 which is arranged in front of the latter and a crystal filter 23 which is arranged in front of the IR cutoff filter 22, wherein intermediate spaces 24 which are filled only with air are provided between the crystal filter 23 and IR cutoff filter 22 and CCD chip 21.

These individual component parts are held by a metal enclosure 25 to which is also fastened a board 26 containing the electrical cables 26' carrying the video signals generated by the CCD chip unit 20.

This CCD chip unit 20 which is shown particularly in FIG. 9 is held in the CCD tube 21 shown in FIG. 8, namely at its distal end 27 which has flexible tongues 28. This assembly is shown again in FIG. 7, wherein the arrangement of the CCD tube 21 in the connection socket 18 provided at its proximal end is also shown, this arrangement being effected by means of a tube clamping socket 29 and a clamping screw 30.

As a result of the spaced construction of the individual parts of the CCD chip unit 20 described above in the silicone substrate 25 and due to the fact that the CCD chip unit 20 is fastened between the tongues 28 of the distal end of the CCD tube 21, the CCD chip unit 20 can behave correspondingly in accordance with its varying expansions corresponding to the temperatures changing during the autoclaving process and subsequent cooling, wherein the tongues 28 ensure that the CCD chip unit 20 is located again in the predetermined area and in the predetermined arrangement at normal temperature.

Figure 5:
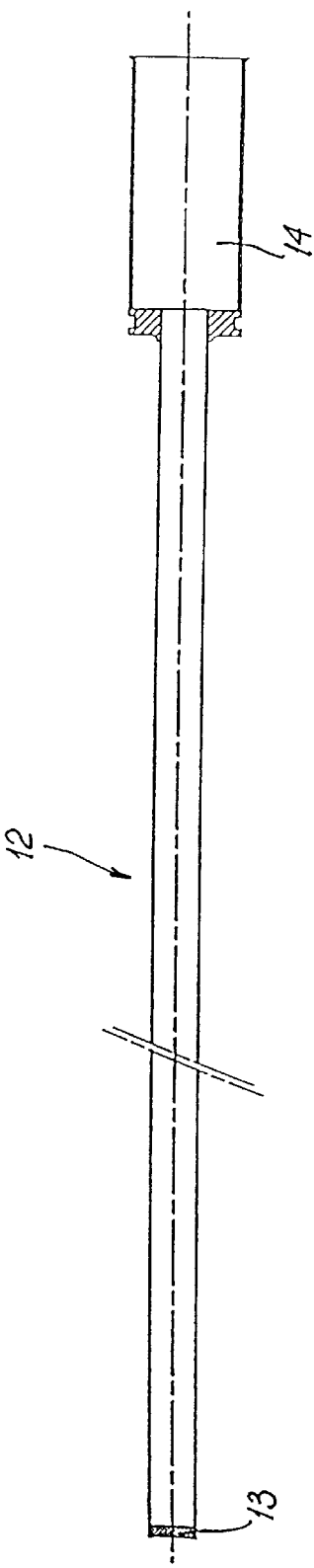
FIG. 5 shows a section through the jacket tube according to illustration d) in FIG. 1.

The CCD-chip tube unit 19 shown in FIG. 7 which includes the CCD tube 21 with connection socket 18 is inserted into the objective unit 15, shown in FIG. 6, from the proximal side. This objective unit 15 substantially comprises the objective tube 17 shown in FIG. 5 and the objective unit 16 which is arranged at the distal end of the objective tube 17 and includes individual objective components.

The endoscope described above is fully autoclavable, namely due to its specially constructed CCD chip unit 20 and also its special arrangement in a CCD tube 21 which is inserted into the objective tube 17 so as to be held in the jacket tube 12 and, together with the latter, as a result of the tight construction of the flat glass 13 arranged at the distal end and the likewise tight construction of the housing socket 14 in combination with the tube clamping socket 29 and the connection socket 18 which is terminated on the outside by a hermetically tight insertion socket system.

The unit described above forms the actual fully autoclavable CCD unit and objective unit which is enclosed by the shaft 1 and the housing 5 of the endoscope.

In addition, the installation of the CCD chip unit 20 between flexible tongues 28 at the distal end 27 of the CCD tube 21 and the fact that this CCD tube 21 is displaceable in the objective tube 17 allows the CCD chip unit 20 to be pulled out of the CCD-chip tube unit 19 in a simple manner and replaced by a new unit when required.

While the foregoing description and drawings represent the preferred embodiments of the present invention, it will be obvious to those skilled in the art that various changes and modifications may be made therein without departing from the true spirit and scope of the present invention.

What is claimed is:

1. An electronic endoscope with a semiconductor image sensor for receiving the images received by an objective and with an electronic circuit, said endoscope comprising:

a shaft with a distal end and a proximal end;

a CCD chip operating as a semiconductor image sensor;

said objective and CCD chip being arranged at said distal end;

a housing for holding the proximal end, said housing also holding the shaft and enclosing a glass-fiber optical connection;

a CCD chip unit, having as component parts a crystal filter, IR cutoff filter and CCD chip, being arranged behind the objective, said component parts being arranged so as to be spaced from one another.

2. The electronic endoscope according to claim 1, wherein the component parts of the CCD chip unit are held in a metal enclosure which forms a component part of the unit and is adjoined by a board having a cable which carries the video signals.

3. The electronic endoscope according to claim 1, wherein the CCD chip unit is held in a resilient or flexible manner at the distal end of a CCD tube.

4. The electronic endoscope according to claim 3, wherein the distal end of the CCD tube has flexible tongues between which the CCD chip unit is held.

5. The electronic endoscope according to claim 1, wherein the shaft of the endoscope has various tubes having small diameters which are adapted to one another and can be inserted one inside the other and are, where appropriate, displaceable relative to one another.

6. The electronic endoscope according to claim 5, wherein the tubes include a CCD tube which holds the CCD chip unit at its distal end in a resilient manner and also contains the board receiving the cables carrying the video signals, an objective tube of larger diameter at whose distal end the objective is arranged, the CCD tube being mounted therein so as to be longitudinally displaceable, and a jacket tube of still larger diameter which receives the CCD tube and the objective tube and which has a flat terminating glass arranged at its distal end.

7. The electronic endoscope according to claim 6, wherein the flat terminating glass is tightly fastened in the jacket tube.

8. The electronic endoscope according to claim 7, wherein the terminating glass at the distal end of the jacket tube is soldered in securely and tightly by means of a solder at 800° C. under a high vacuum.

9. The electronic endoscope according to claim 6, wherein the jacket tube has, at its proximal end, a housing socket into which a tube clamping socket projects, this tube clamping socket being connected with the CCD tube via a clamping screw, and wherein a connection socket having a hermetically tight insertion connection or plug-in connection and forming the closure of the proximal end of the jacket tube is arranged in the tube clamping socket.

10. The electronic endoscope according to claim 1, wherein each of the surfaces of the structural component parts of the CCD chip unit is provided with an anti-reflection agent coating.

* * * * *